United States Patent
McHenry et al.

(10) Patent No.: US 11,129,667 B2
(45) Date of Patent: Sep. 28, 2021

(54) SYSTEMS AND METHODS FOR CONTROLLING POWER IN AN ELECTROSURGICAL GENERATOR

(71) Applicant: Covidien LP, Mansfield, MA (US)

(72) Inventors: Jennifer R. McHenry, Denver, CO (US); Alexander M. Waskiewicz, Lafayette, CO (US); Anthony D. Ricke, Boulder, CO (US); Rebecca J. Coulson, Lyons, CO (US); Jessica E. C. Olson, Frederick, CO (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/847,778

(22) Filed: Apr. 14, 2020

(65) Prior Publication Data

US 2020/0237427 A1    Jul. 30, 2020

Related U.S. Application Data (62) Division of application No. 15/133,985, filed on Apr. 20, 2016, now Pat. No. 10,617,463.

(Continued)

(51) Int. Cl.
*A61B 18/18* (2006.01)
*A61B 18/12* (2006.01)
(Continued)

(52) U.S. Cl.
CPC ...... *A61B 18/1233* (2013.01); *A61B 18/1445* (2013.01); *A61B 18/1206* (2013.01);
(Continued)

(58) Field of Classification Search
CPC ............ A61B 18/1233; A61B 18/1455; A61B 18/1206; A61B 2018/0063;
(Continued)

(56) References Cited

U.S. PATENT DOCUMENTS 5,472,443 A    12/1995   Cordis et al.
6,080,149 A    6/2000    Huang et al.
(Continued)

FOREIGN PATENT DOCUMENTS

DE    179607 C    11/1906
DE    390937 C    3/1924
(Continued)

OTHER PUBLICATIONS

Wald et al., "Accidental Burns", JAMA, Aug. 16, 1971, vol. 217, No. 7, pp. 916-921.
(Continued)

*Primary Examiner* — Jaymi E Della
*Assistant Examiner* — Rachel A. Vierra
(74) *Attorney, Agent, or Firm* — Carter, DeLuca & Farrell LLP (57) ABSTRACT

The electrosurgical systems and corresponding methods of the present disclosure involve an electrosurgical generator, sensing circuitry, and a controller. The electrosurgical generator includes a radio frequency (RF) output stage that supplies power to tissue. The sensing circuitry measures impedance of tissue. The controller controls the power supplied from the RF output stage to track a nonlinear power curve until the power supplied from the RF output stage has reached a predetermined peak power of the nonlinear power curve. The controller further determines whether a tissue reaction has occurred based on impedance measured by the sensing circuitry and controls the power supplied from the RF output stage during a cooling phase if the controller determines that a tissue reaction has occurred. The controller may further control the power supplied from the RF output stage to track a linear power curve.

18 Claims, 6 Drawing Sheets

Related U.S. Application Data (60) Provisional application No. 62/151,655, filed on Apr. 23, 2015.

(51) Int. Cl.
*A61B 18/14* (2006.01)
*A61B 18/00* (2006.01)

(52) U.S. Cl.
CPC .......... *A61B 2018/0063* (2013.01); *A61B 2018/00589* (2013.01); *A61B 2018/00642* (2013.01); *A61B 2018/00702* (2013.01); *A61B 2018/00875* (2013.01); *A61B 2018/00988* (2013.01); *A61B 2018/126* (2013.01); *A61B 2018/1823* (2013.01)

(58) Field of Classification Search
CPC ........... A61B 2018/00589; A61B 2018/00642; A61B 2018/00702; A61B 2018/00875; A61B 2018/126; A61B 2018/1823
See application file for complete search history.

(56) References Cited

U.S. PATENT DOCUMENTS

| | | | |
|---|---|---|---|
| 6,468,270 | B1 | 10/2002 | Hovda et al. |
| 6,837,888 | B2 | 1/2005 | Ciarrocca et al. |
| 6,942,660 | B2 | 9/2005 | Pantera et al. |
| 6,974,453 | B2 | 12/2005 | Woloszko et al. |
| D574,323 | S | 8/2008 | Waaler |
| 7,901,400 | B2 | 3/2011 | Wham et al. |
| 9,270,202 | B2 | 2/2016 | Johnson et al. |
| 9,283,028 | B2 | 3/2016 | Johnson |
| 2002/0029036 | A1 | 3/2002 | Goble et al. |
| 2002/0133152 | A1* | 9/2002 | Strul .............. A61B 18/1445 606/50 |
| 2002/0165531 | A1 | 11/2002 | Goble |
| 2004/0167508 | A1 | 8/2004 | Wham et al. |
| 2005/0203504 | A1 | 9/2005 | Wham et al. |
| 2006/0217707 | A1 | 9/2006 | Daniel et al. |
| 2007/0173811 | A1 | 7/2007 | Couture et al. |
| 2007/0265616 | A1 | 11/2007 | Couture et al. |
| 2008/0221565 | A1 | 9/2008 | Eder et al. |
| 2008/0287944 | A1 | 11/2008 | Pearson et al. |
| 2009/0240244 | A1 | 9/2009 | Malis et al. |
| 2011/0028963 | A1 | 2/2011 | Gilbert |
| 2011/0037484 | A1 | 2/2011 | Gilbert |
| 2011/0038056 | A1 | 2/2011 | Nakamura |
| 2011/0208183 | A1 | 8/2011 | Stockert |
| 2012/0078139 | A1 | 3/2012 | Aldridge et al. |
| 2012/0101413 | A1 | 4/2012 | Beetel |
| 2012/0136354 | A1 | 5/2012 | Rupp |
| 2012/0179154 | A1 | 7/2012 | Goldberg et al. |
| 2012/0283731 | A1* | 11/2012 | Unger .............. A61B 18/1206 606/49 |
| 2014/0100559 | A1 | 4/2014 | Wham et al. |
| 2014/0232463 | A1 | 8/2014 | Gilbert |
| 2014/0243815 | A1 | 8/2014 | Kerr |
| 2014/0253140 | A1 | 9/2014 | Gilbert |
| 2014/0257270 | A1 | 9/2014 | Behnke |
| 2014/0258800 | A1 | 9/2014 | Gilbert |
| 2014/0276659 | A1 | 9/2014 | Juergens et al. |
| 2014/0276750 | A1 | 9/2014 | Gilbert |
| 2014/0276753 | A1 | 9/2014 | Wham et al. |
| 2014/0276754 | A1 | 9/2014 | Gilbert et al. |
| 2014/0358138 | A1 | 12/2014 | Mattmiller et al. |
| 2014/0376269 | A1 | 12/2014 | Johnson et al. |
| 2015/0025521 | A1 | 1/2015 | Friedrichs et al. |
| 2015/0025523 | A1 | 1/2015 | Friedrichs et al. |
| 2015/0032096 | A1 | 1/2015 | Johnson |
| 2015/0032098 | A1 | 1/2015 | Larson et al. |
| 2015/0032099 | A1 | 1/2015 | Larson et al. |
| 2015/0032100 | A1 | 1/2015 | Coulson et al. |
| 2015/0088116 | A1 | 3/2015 | Wham |
| 2015/0088117 | A1 | 3/2015 | Gilbert et al. |
| 2015/0088118 | A1 | 3/2015 | Gilbert et al. |
| 2015/0088124 | A1 | 3/2015 | Wham |
| 2015/0088125 | A1 | 3/2015 | Wham |
| 2015/0119871 | A1 | 4/2015 | Johnson et al. |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 0246350 A1 | 11/1987 |
| EP | 0267403 A2 | 5/1988 |
| EP | 0296777 A2 | 12/1988 |
| EP | 0310431 A2 | 4/1989 |
| EP | 0325456 A2 | 7/1989 |
| EP | 0336742 A2 | 10/1989 |
| EP | 0390937 A1 | 10/1990 |
| EP | 0556705 A1 | 8/1993 |
| EP | 0608609 A2 | 8/1994 |
| EP | 0836868 A2 | 4/1998 |
| EP | 0880220 A2 | 11/1998 |
| EP | 0882955 A1 | 12/1998 |
| EP | 1051948 A2 | 11/2000 |
| EP | 1366724 A1 | 12/2003 |
| EP | 1776929 A1 | 4/2007 |
| EP | 2111812 A2 | 10/2009 |
| EP | 2649956 A1 | 10/2013 |
| FR | 1275415 A | 11/1961 |
| FR | 1347865 A | 1/1964 |
| FR | 2313708 A1 | 12/1976 |
| FR | 2364461 A1 | 4/1978 |
| FR | 2502935 A1 | 10/1982 |
| FR | 2517953 A1 | 6/1983 |
| FR | 2573301 A1 | 5/1986 |
| JP | 63005876 | 1/1988 |
| JP | 2002065690 A | 3/2002 |
| JP | 2005185657 A | 7/2005 |
| SU | 166452 | 11/1964 |
| SU | 727201 A2 | 4/1980 |
| WO | 0211634 A1 | 2/2002 |
| WO | 0245589 A2 | 6/2002 |
| WO | 03090635 A1 | 11/2003 |
| WO | 2006050888 A1 | 5/2006 |
| WO | 2008053532 A1 | 5/2008 |
| WO | 2008071914 A2 | 6/2008 |

OTHER PUBLICATIONS

Vallfors et al., "Automatically Controlled Bipolar Electrosoagulation—'COA-COMP'", Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Prutchi et al. "Design and Development of Medical Electronic Instrumentation", John Wiley & Sons, Inc. 2005.

(56) References Cited

OTHER PUBLICATIONS

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System" Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf- >, pp. 6, 11, 73.
Ogden, "Goertzel Alternative to the Fourier Transform": Jun. 1993 pp. 485-487 Electronics World; Reed Business Publishing, Sutton, Surrey, BG, vol. 99, No. 9, 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al.. "The Measurement of Physiologic Events by Electrical Impedence" Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994), pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B. V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
Extended European Search Report for EP 14 17 7968 dated Oct. 13, 2014.
Extended European Search Report for EP 16 16 6711 dated Sep. 29, 2016.

* cited by examiner

SYSTEMS AND METHODS FOR CONTROLLING POWER IN AN ELECTROSURGICAL GENERATOR

CROSS REFERENCE TO RELATED APPLICATIONS

This application is a divisional application of U.S. patent application Ser. No. 15/133,985, filed on Apr. 20, 2016, which claims the benefit of and priority to U.S. Provisional Patent Application No. 62/151,655, filed on Apr. 23, 2015. The entire contents of each of the foregoing applications are hereby incorporated by reference herein.

BACKGROUND

Technical Field

The present disclosure relates to electrosurgical systems and methods for performing electrosurgery. More particularly, the present disclosure relates to controlling the delivery of power to tissue during the cook stage of a tissue sealing procedure.

Description of Related Art

Electrosurgery involves application of high radio frequency (RF) electrical current to a surgical site to seal, cut, ablate, or coagulate tissue. In monopolar electrosurgery, a source or active electrode delivers RF energy from the electrosurgical generator to the tissue and a return electrode (e.g., a return pad) carries the current back to the generator. In monopolar electrosurgery, the active electrode is typically part of the surgical instrument held by the surgeon and applied to the tissue to be treated. The patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

Bipolar electrosurgery generally involves the use of forceps. A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to affect hemostasis on the clamped tissue. The forceps include electrosurgical conductive plates which apply electrosurgical energy to the clamped tissue. By controlling the intensity, frequency and duration of the electrosurgical energy applied through the conductive plates to the tissue, the surgeon can coagulate, cauterize and/or seal tissue.

Tissue or vessel sealing is a process of liquefying the collagen, elastin, and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Tissue sealing procedures involve more than simply cauterizing or coagulating tissue to create an effective seal; the procedures involve precise control of a variety of factors. For example, in order to affect a proper seal in vessels or tissue, two predominant mechanical parameters must be accurately controlled: the pressure applied to the tissue and the gap distance between the electrodes (i.e., the distance between opposing jaw members or opposing sealing plates). In addition, electrosurgical energy must be applied to the tissue under controlled conditions to ensure the creation of an effective vessel seal. Techniques have been developed to control or vary the power of energy applied to the tissue during the tissue sealing process. When a target tissue impedance threshold is reached, the tissue seal is deemed completed and the delivery of electrosurgical energy is halted.

The power control systems of conventional electrosurgical generators include nonlinearities that may impact the quality and consistency of tissue seals. To overcome these nonlinearities, electrosurgical generators have been designed to include high performance control systems. These high performance control systems use field-programmable gate array (FPGAs) technology to allow for increased generator control speeds so that the high performance control systems can overcome the nonlinearities of conventional power control systems.

SUMMARY

The present disclosure features an electrosurgical generator, comprising, a radio frequency (RF) output stage that supplies power to tissue; sensing circuitry that measures impedance of tissue; and a controller which controls the power supplied from the RF output stage to track a nonlinear power curve until the power supplied from the RF output stage has reached a predetermined peak power of the nonlinear power curve; determine whether a tissue reaction has occurred based on impedance measured by the sensing circuitry; and control the power supplied from the RF output stage during a cooling phase if the controller determines that a tissue reaction has occurred.

In one aspect, the controller further controls the power supplied from the RF output stage to track a linear power curve if the controller determines that the power supplied from the RF output stage has reached the predetermined peak power of the nonlinear power curve. In another aspect, the controller includes a memory storing a look-up table including a plurality of nonlinear power curves, a respective plurality of linear power curves, and a respective plurality of sizes of electrodes of electrosurgical instruments usable with the electrosurgical generator, and the controller receives an electrode size and selects a nonlinear power curve from the plurality of nonlinear power curves and a respective linear power curve from the plurality of linear power curves based on the received electrode size.

In other aspects, the controller further adjusts a parameter of the linear power curve based on a surface area of an electrode of an electrosurgical instrument usable with the electrosurgical generator. In other aspects, the parameter of the linear power curve is selected from the group consisting of slope and duration. In other aspects, the duration of the linear power curve is zero. In other aspects, the linear power curve has a shorter duration and a larger slope for a larger surface area of the electrode. In other aspects, the linear power curve has a longer duration and a smaller slope for a smaller surface area of the electrode.

In other aspects, the controller further adjusts a parameter of the nonlinear power curve based on a surface area of an electrode of an electrosurgical instrument usable with the electrosurgical generator. In other aspects, the parameter of the nonlinear power curve is selected from the group consisting of starting power, duration, shape, slopes, the predetermined peak power, and combinations thereof. In other aspects, the nonlinear power curve has a longer duration and a smaller predetermined peak power for a larger surface area of the electrode. In other aspects, the nonlinear power curve has a shorter duration and a larger predetermined peak power for a smaller surface area of the electrode. In further aspects, the electrosurgical instrument includes a Radio Frequency Identification tag storing the parameter of the nonlinear power curve. In another aspect, the nonlinear power curve is a third-order or cubic polynomial defined by a plurality of coefficients.

In other aspects, the controller determines a minimum impedance based on the measured impedance. In other aspects, the controller further determines whether a tissue reaction has occurred based on the minimum impedance and a predetermined rise in impedance of tissue being treated. In other aspects, the controller further determines whether a tissue reaction has occurred within a first predetermined period, stop the power supplied from the RF output stage, and issue a re-grasp message, if the controller determines that a tissue reaction has occurred within the first predetermined period. In other aspects, the controller further determines whether a tissue reaction has occurred within a second predetermined period, and control the power supplied from the RF output stage to restart tracking of the nonlinear power curve if the controller determines that a tissue reaction has not occurred within the second predetermined period. Any one or more of the above aspects of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, wherein.

DETAILED DESCRIPTION

The electrosurgical systems and methods of the present disclosure control the power of electrosurgical energy output from an electrosurgical generator so that the power follows or tracks power control curves having a non-linear power control curve and a linear power control curve during a "cook stage" of an electrosurgical procedure. These power control curves stem from the observation that tissue volume and the electrosurgical energy required to heat that tissue volume have a non-linear relationship. According to embodiments of the present disclosure, the non-linear power control curve, such as a polynomial power control curve, is tuned to provide an initially low rate of increase of power to the tissue, but later compensates for the low rate of increase of power by a higher rate of increase of power.

Figure 1A:
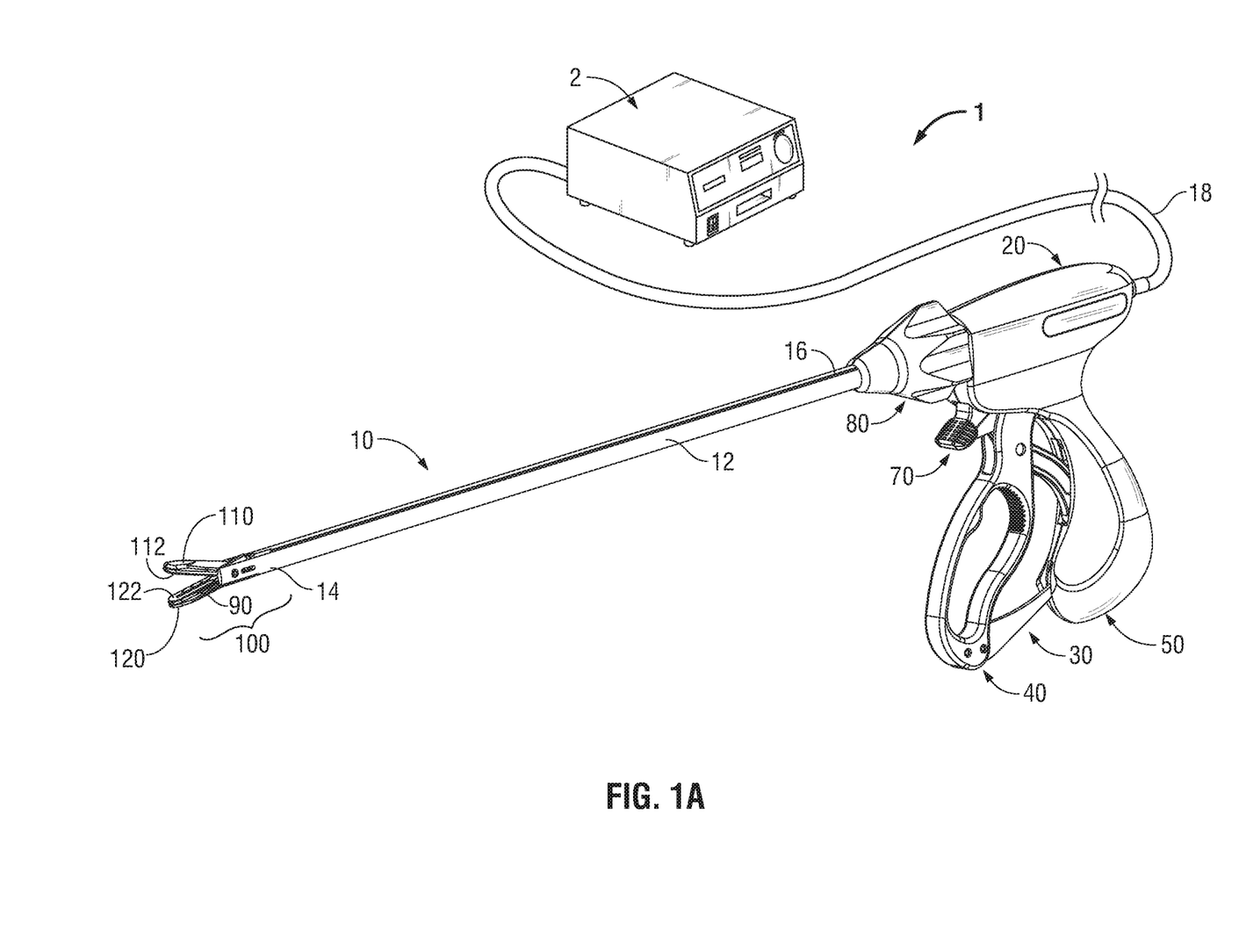
FIG. 1A is a perspective view of an electrosurgical system including an electrosurgical generator and an electrosurgical instrument having an end effector, according to embodiments of the present disclosure.

FIG. 1A is a schematic illustration of an electrosurgical system 1. Electrosurgical system 1 includes forceps 10 for treating patient tissue. Electrosurgical energy is supplied to forceps 10 by an electrosurgical generator 2 via a cable 18. This allows the user to selectively coagulate and/or seal tissue.

As shown in FIG. 1A, forceps 10 is an endoscopic version of a vessel sealing bipolar forceps. Forceps 10 is configured to support an end effector assembly 100 and generally includes a housing 20, a handle assembly 30, a rotating assembly 80, and a trigger assembly 70 that mutually cooperate with the end effector assembly 100 to grasp, seal, and if required, divide tissue. Forceps 10 also includes a shaft 12 that has a distal end 14, which mechanically engages the end effector assembly 100, and a proximal end 16 which mechanically engages the housing 20 proximate to the rotating assembly 80.

Figure 1B:
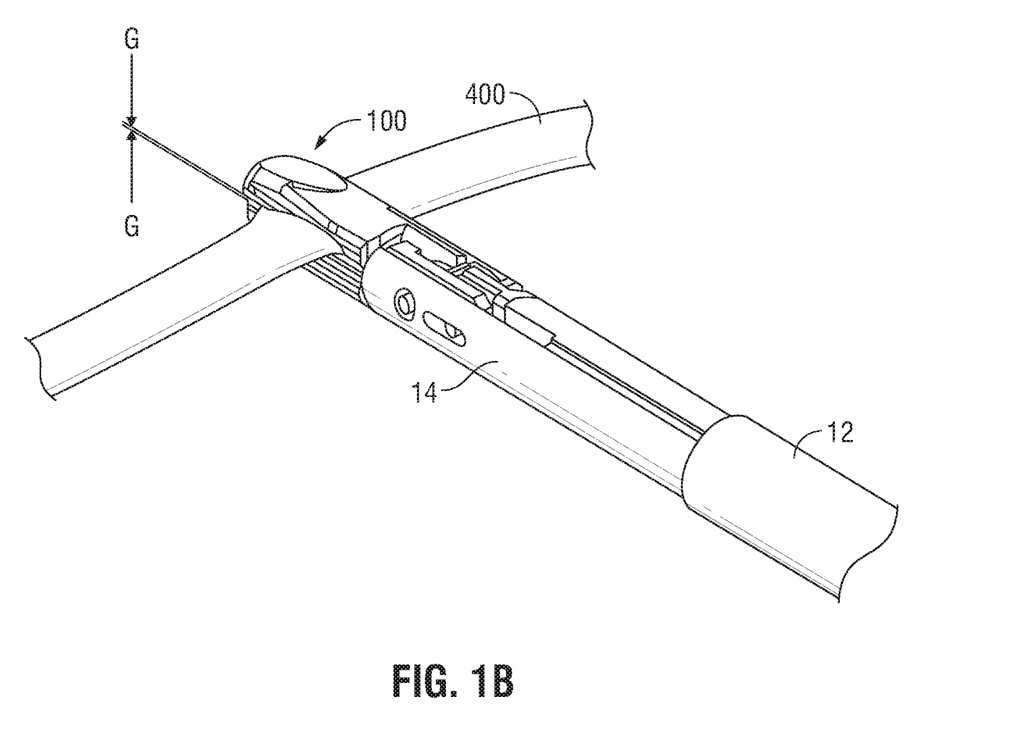
FIG. 1B is a rear, perspective view of the end effector of FIG. 1A shown with tissue disposed between the jaw members of the end effector.

Forceps 10 also includes a plug (not shown) that connects forceps 10 to a source of electrosurgical energy, e.g., electrosurgical generator 2, via cable 18. Handle assembly 30 includes a fixed handle 50 and a movable handle 40. Handle 40 moves relative to fixed handle 50 to actuate the end effector assembly 100 and enable a user to selectively grasp and manipulate tissue 400, as shown in FIG. 1B. Forceps 10 may also include an identification module (not explicitly shown) such as a resistor or computer memory or a Radio-frequency identification (RFID) or barcode readable by the generator 2 to identify the forceps.

Referring to FIGS. 1A and 1B, end effector assembly 100 includes a pair of opposing jaw members 110 and 120. Electrically conductive sealing plates 112 and 122 are attached to jaw members 110 and 120, respectively. Electrically conductive sealing plates 112 and 122 conduct electrosurgical energy through tissue 400 held between jaw members 110 and 120. Jaw members 110 and 120 move in response to movement of handle 40 from an open position to a closed position. In the open position, electrically conductive sealing plates 112 and 122 are disposed in spaced relation relative to one another. In the closed or clamping position, electrically conductive sealing plates 112 and 122 cooperate to grasp tissue and apply electrosurgical energy to the grasped tissue. In embodiments, end effector assembly 100 includes a jaw angle sensor (not shown) adapted to sense the angle 114 between jaw members 110 and 120 and configured to operably couple to electrosurgical generator 2.

Jaw members 110 and 120 are activated using a drive assembly (not shown) enclosed within the housing 20. The drive assembly cooperates with the movable handle 40 to move jaw members 110 and 120 from the open position to the closed position. Examples of handle assemblies are shown and described in commonly-owned U.S. Pat. No. 7,156,846 entitled "VESSEL SEALER AND DIVIDER FOR USE WITH SMALL TROCARS AND CANNULAS," the contents of which are hereby incorporated by reference herein in their entirety.

The handle assembly 30 may include a four-bar mechanical linkage which provides a unique mechanical advantage when sealing tissue between jaw members 110 and 120. For example, once the desired position for the sealing site is determined and jaw members 110 and 120 are properly positioned, handle 40 may be compressed fully to lock electrically conductive sealing plates 112 and 122 in a closed position against the tissue. The details relating to the inter-cooperative relationships of the inner-working components of forceps 10 are disclosed in the above-cited commonly-owned U.S. Pat. No. 7,156,846, which discloses an off-axis, lever-like handle assembly.

Forceps 10 also includes a rotating assembly 80 mechanically associated with the shaft 12 and the drive assembly (not shown). Movement of the rotating assembly 80 imparts similar rotational movement to the shaft 12 which, in turn, rotates the end effector assembly 100. Various features along with various electrical configurations for the transference of electrosurgical energy through the handle assembly 30 and the rotating assembly 80 are described in more detail in the above-mentioned commonly-owned U.S. Pat. No. 7,156,846.

As shown in FIGS. 1A and 1B, end effector assembly 100 attaches to the distal end 14 of shaft 12. Jaw members 110 and 120 are pivotable about a pivot 160 from the open to closed positions upon relative reciprocation, i.e., longitudinal movement, of the drive assembly (not shown). Again, examples of mechanical and cooperative relationships with respect to the various moving elements of the end effector assembly 100 are further described in the above-mentioned commonly-owned U.S. Pat. No. 7,156,846.

Forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 20 and handle assembly 30. In either of these two instances, forceps 10 may be either partially disposable or replaceable, such as where a new or different end effector assembly 100 or end effector assembly 100 and shaft 12 are used to selectively replace the old end effector assembly 100 as needed.

The electrosurgical generator 2 includes input controls (e.g., buttons, activators, switches, touch screen, etc.) for controlling the generator. In addition, the electrosurgical generator 2 includes one or more display screens for providing the surgeon with a variety of output information (e.g., intensity settings, treatment complete indicators, etc.). The controls allow the surgeon to adjust parameters of the RF energy output by the electrosurgical generator 2, including the power and the waveform, to achieve a desired result suitable for a particular task (e.g., coagulating, tissue sealing, division with hemostatis, etc.). Forceps 10 may include a plurality of input controls which may be redundant with certain input controls of the electrosurgical generator 2. Placing the input controls at forceps 10 allows for easier and faster modification of RF energy parameters during the surgical procedure without requiring interaction with the electrosurgical generator 2.

Figure 2:
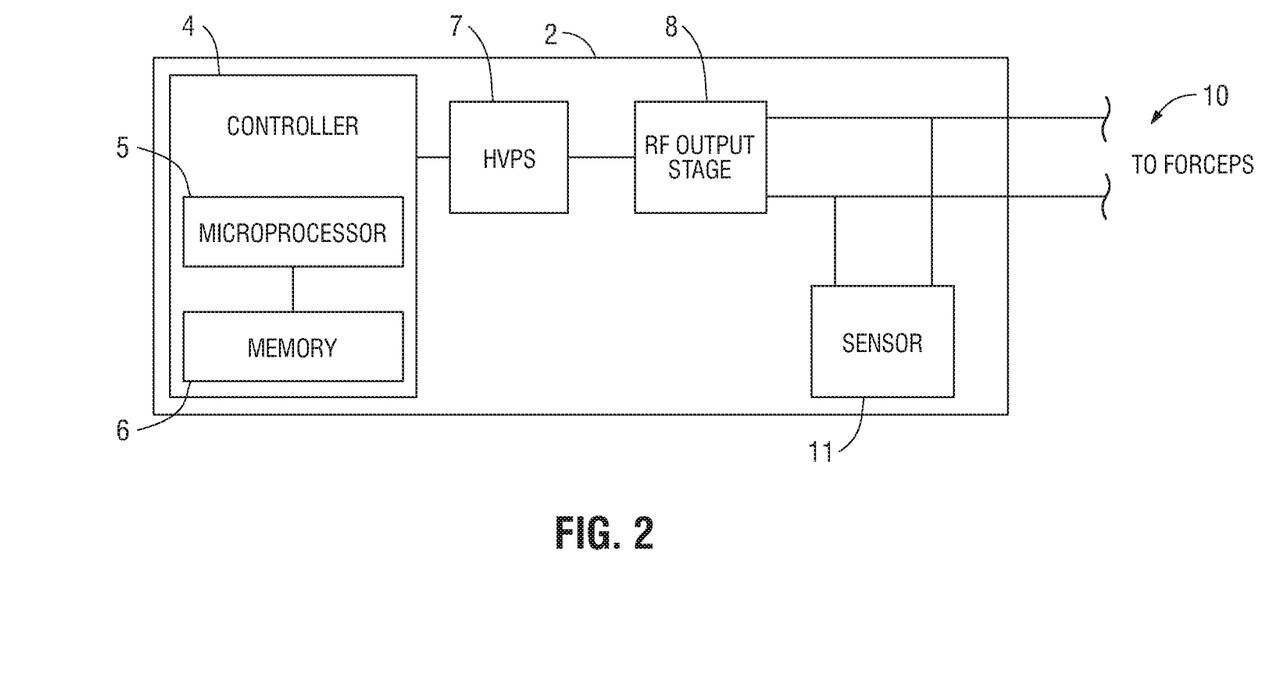
FIG. 2 is a schematic block diagram of a generator control system according to the present disclosure.

FIG. 2 shows a schematic block diagram of the electrosurgical generator 2 having a controller 4, a high voltage DC power supply 7 ("HVPS"), an RF output stage 8, and sensor circuitry 11. HVPS 7 provides DC power to an RF output stage 8 which then converts DC power into RF energy and delivers the RF energy to forceps 10. Controller 4 includes a microprocessor 5 operably connected to a memory 6 which may be volatile type memory (e.g., RAM) and/or non-volatile type memory (e.g., flash media, disk media, etc.). Microprocessor 5 includes an output port which is operably connected to the HVPS 7 and/or RF output stage 8 allowing the microprocessor 5 to control the output of the generator 2 according to either open and/or closed control loop schemes. A closed loop control scheme may be a feedback control loop wherein the sensor circuitry 11 provides feedback to controller 4 (i.e., information obtained from one or more of sensing mechanisms for sensing various tissue parameters such as tissue impedance, tissue temperature, fluid presence, output current and/or voltage, etc.). Controller 4 then signals the HVPS 7 and/or RF output stage 8 which then adjusts DC power supply and/or RF power supply, respectively. The controller 4 also receives input signals from the input controls of the generator 2 and/or forceps 10. Controller 4 utilizes the input signals to adjust the power output of the generator 2 and/or instructs generator 2 to perform other control functions.

It is known that sealing of the tissue 400 is accomplished by virtue of a unique combination of gap control, pressure, and electrical control. In particular, controlling the intensity, frequency, and duration of the electrosurgical energy applied to the tissue through the electrically conductive sealing plates 112 and 122 are important electrical considerations for sealing tissue. In addition, two mechanical factors play an important role in determining the resulting thickness of the sealed tissue and the effectiveness of the seal, i.e., the pressure applied between jaw members 110 and 120 (between about 3 kg/cm2 to about 16 kg/cm2) and the gap distance "G" between electrically conductive sealing plates 112 and 122 of jaw members 110 and 120, respectively, during the sealing process (between about 0.001 inches to about 0.006 inches). One or more stop members 90 may be employed on one or both sealing plates to control the gap distance. A third mechanical factor that contributes to the quality and consistency of a tissue seal is the closure rate of the electrically conductive surfaces or sealing plates during electrical activation.

Figure 4:
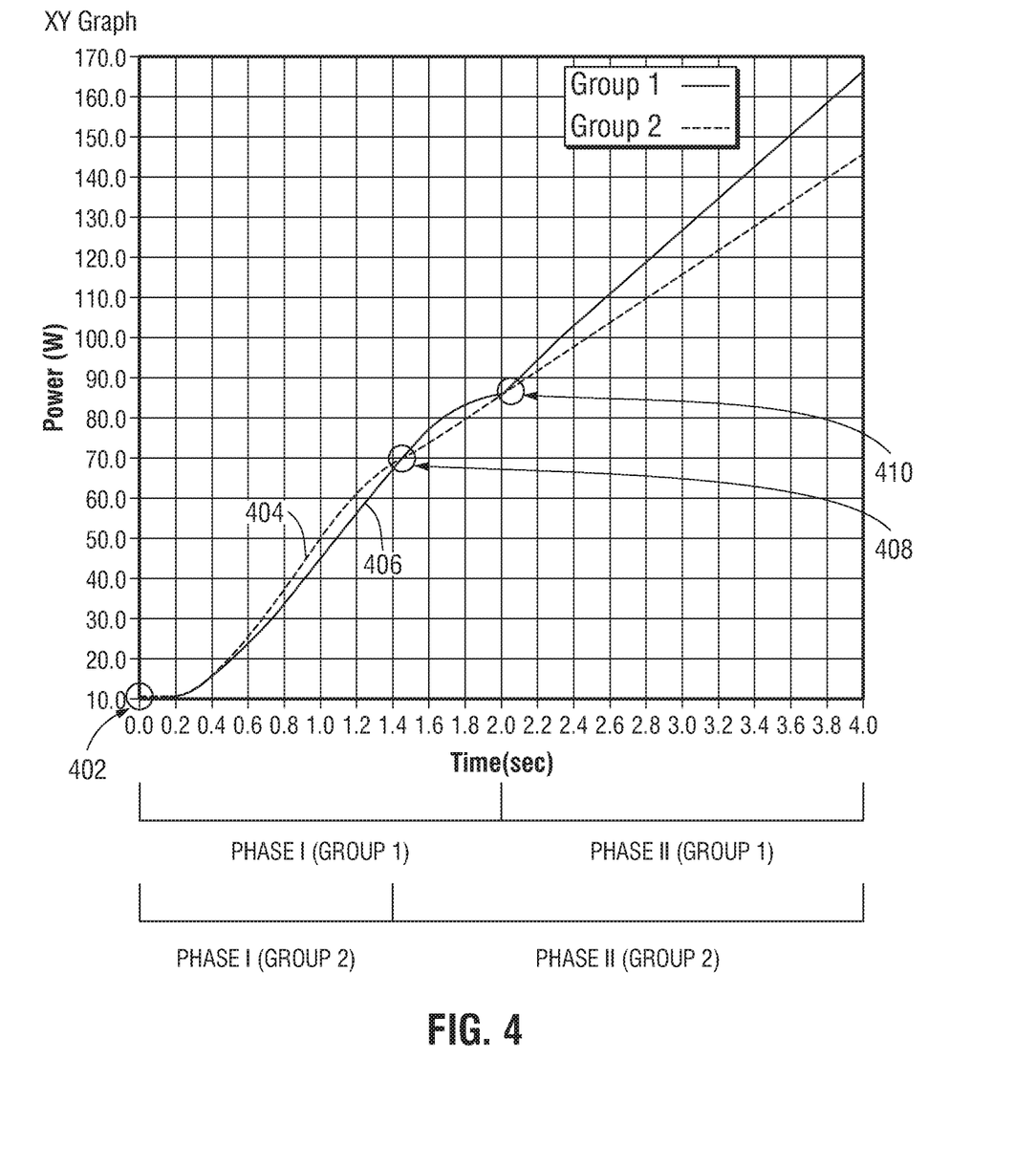
FIG. 4 is a graph illustrating changes in supplied energy during a sealing procedure utilizing the method shown in FIGS. 3A and 3B.

Since forceps 10 applies energy through electrodes, each of jaw members 110 and 120 includes a pair of electrically conductive sealing plates 112, 122, respectively, disposed on an inner-facing surface thereof. Thus, once jaw members 110 and 120 are fully compressed about tissue 400, forceps 10 is ready for selective application of electrosurgical energy as shown in FIG. 4. Upon the application of electrosurgical energy, electrically conductive sealing plates 112 and 122 cooperate to seal tissue 400 held between electrically conductive sealing plates 112 and 122.

Electrosurgical system 1 according to the present disclosure regulates application of energy and pressure to achieve an effective seal capable of withstanding high burst pressures. Electrosurgical generator 2 applies energy to tissue during the cook stage based on a power control curve or a current control curve. Two examples of power control curves are illustrated in FIG. 4. Power control curve 404 may be used for smaller-sized jaw members while power control curve 406 may be used for larger-sized jaw members. As described below, the point of transition from the polynomial portion of the power control curve to the linear portion of the power control curve (e.g., at the peak of the polynomial portion) and/or other parameters of the power control curve may be adjusted as a function of the size of jaw members 110 and 120.

A RFID or barcode tag may be attached to one of jaw members 110 and 120 to provide the parameters for the power control curve, For example, through the use of the RFID or barcode tags, electrical generator 2 may use the specific information found in the RFID or barcode tag to select from a lookup table the parameters for the power control curve prior to application of the power. The parameters used in implementation of the power control curve which controller 4 tracks include but are not limited to: the peak of the polynomial portion of the power control curve or the point of transition from the polynomial portion of the power control curve to the linear portion of the power control curve, the minimum starting power of the power control, the coefficients (e.g., a, b, c, and d used in equation (1) below), minimum time during the polynomial portion of the power curve or minimum time during the cook stage, slope of the linear portion of the power control curve, The control system of the present disclosure includes controller 4 and memory 6. This control system regulates the electrosurgical energy output by the RF output stage 8. For example, the control system may vary characteristics of the electrosurgical energy (e.g., power, voltage being maintained, duration of power application, etc.) based on the type of tissue being sealed. The control system may vary the duration of the application of power depending on the size, thickness, or other characteristics of the tissue. For example, the control system may use a longer duration of the application of power for thicker tissue or a shorter duration of the application of power for thinner tissue. In embodiments, the control system may adjust the power of the electrosurgical energy based on the jaw angle.

As mentioned above, various methods and devices are contemplated to automatically regulate the closure of jaw members 110 and 120 about tissue to keep the pressure constant during the sealing process. For example, forceps 10 may be configured to include a ratchet mechanism (not explicitly shown) which initially locks jaw members 110 and 120 against the tissue under a desired tissue pressure and then increases the pressure according to the command from the microprocessor 5 to an optimum tissue pressure. The ratchet mechanism (not explicitly shown) is configured to adjust the pressure based on electrical activation and/or the tissue reaction. The pressure may be controlled in a similar manner towards the end of the seal cycle, i.e., release pressure. The pressure may be held constant or varied during a cooling period. A similar or the same ratchet mechanism (not explicitly shown) may be employed for this purpose as well. The ratchet mechanism (not explicitly shown) may be configured to automatically release or unlock at the end of a cooling period. Other controllable closure mechanisms or pressure-applying mechanism are also envisioned which may be associated with the handle assembly 30, the housing 20 and/or jaw members 110 and 120. Any of these mechanisms may be housed in the housing 20 or form a part of each particular structure. The ratchet, closure, and/or pressure-applying mechanism may include any suitable actuating device, for example without limitation, a solenoid, stepper motor, vacuum actuator, and/or a pressure actuator.

From the foregoing and with reference to the various drawings, those skilled in the art will appreciate that certain modifications can also be made to the present disclosure without departing from the scope of the same. Further details relating to one particular open forceps are disclosed in commonly-owned U.S. Pat. No. 7,811,283 entitled "OPEN VESSEL SEALING INSTRUMENT WITH CUTTING MECHANISM AND DISTAL LOCKOUT," the entire contents of which are incorporated by reference herein.

Figure 3A:
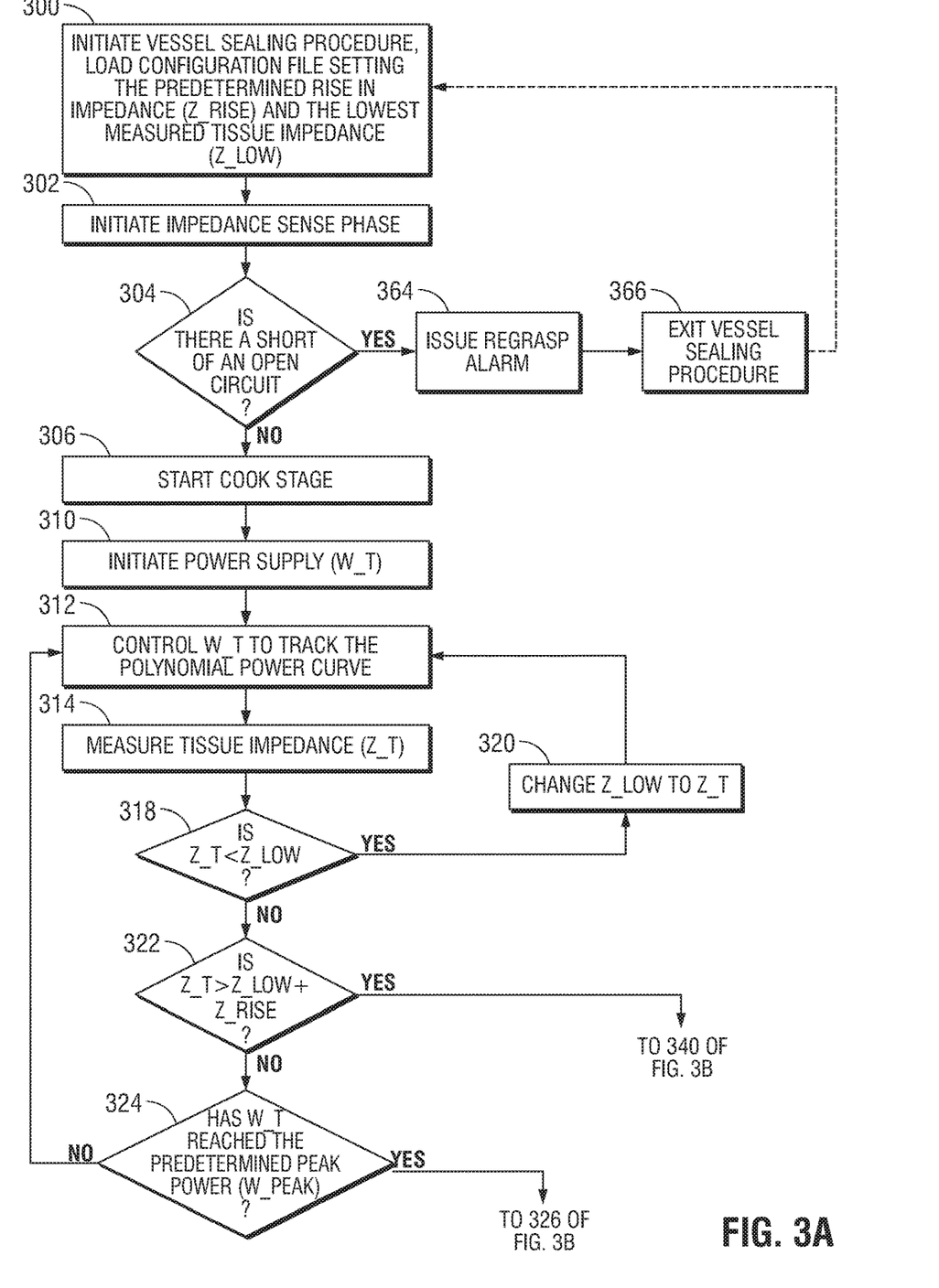
FIG. 3A is a flow chart showing a first portion of a tissue sealing method according to embodiments of the present disclosure.
Figure 3B:
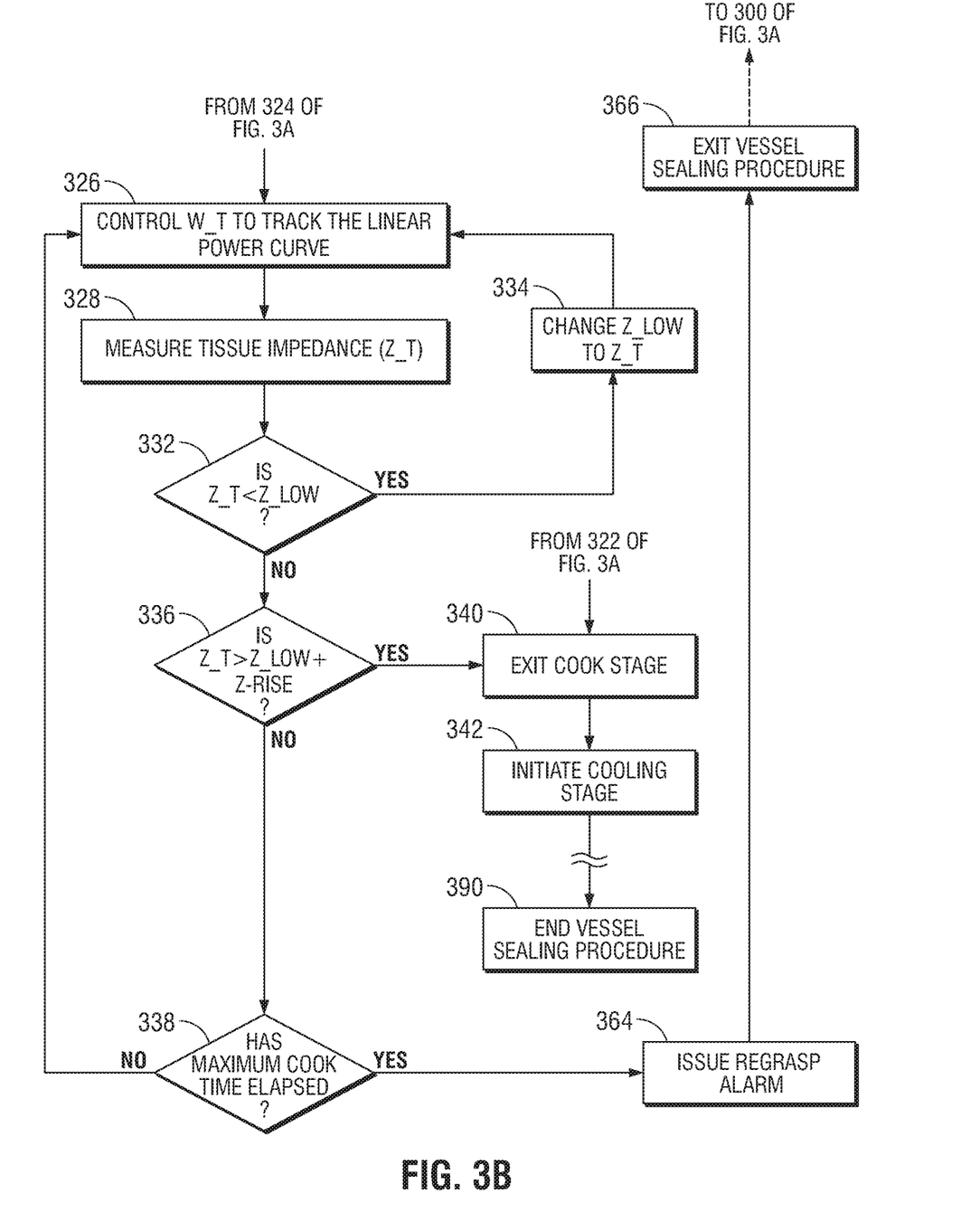
FIG. 3B is a flow chart showing a second portion of a tissue sealing method according to embodiments of the present disclosure.

FIGS. 3A and 3B are a flowchart illustrating a first and second portion of a tissue sealing process according to embodiments of the present disclosure. In step 300, the tissue sealing procedure is activated (e.g., by pressing of a foot pedal or hand-switch) and a host processor (e.g., microprocessor 5) activates a tissue sealing control system and loads a configuration file, e.g., from the generator's internal memory or from an RFID tag attached to the instrument or forceps. The configuration file includes settings for the control system, e.g., an end impedance threshold (e.g., EndZ), baseline cooling time (e.g., Base Cool T), a forceps/instrument identification (e.g., ForcepsID), and coefficients defining the power curve for the cook stage. At least some of the settings may depend on the tissue type. In embodiments, the configuration file may include settings corresponding to different tissue types. In those embodiments, when the control system determines the tissue type, e.g., through user input or by using a detector that detects tissue type, the control system selects settings for the determined tissue type. In embodiments, some of the settings of the configuration file may be adjusted based on the instrument being used or the settings selected by a surgeon.

The configuration file may be loaded from a data store included within controller 4. Additionally or alternatively, the configuration file may be loaded from a data store, e.g., a nonvolatile memory or RFID tag, included within forceps 10. In embodiments, a plurality of configuration files may be included within controller 4. A configuration file may be selected and loaded in accordance with the type of forceps being utilized, e.g., as determined based on the ForcepsID. In embodiments, forceps 10 are interrogated by controller 4 to ascertain the ForcepsID, whereupon a configuration file corresponding to the ForcepsID is loaded. The baseline cooling time may be determined in accordance with ForcepsID. In step 300, the predetermined impedance rise value (e.g., Z_Rise) is loaded from the configuration file. The predetermined impedance rise value (Z_Rise) value may range from about 1 ohm to about 750 ohms and its specific value is based on the electrosurgical generator 2 used and tissue being sealed. Additionally, in step 300, the control system records the lowest impedance value (e.g., Z_Low) based on the measured impedance and stores the lowest impedance value (Z_Low) in memory.

In step 302, the process begins with an impedance sense phase. In step 302, the process measures the tissue impedance using an interrogatory impedance sensing pulse of a predetermined duration, e.g., approximately 100 ms. The value of the median measured tissue impedance is stored as a start impedance value (e.g., Start Z). Tissue impedance is determined without appreciably changing the tissue. During this interrogation or error-checking phase, the electrosurgical generator 2 checks for an open circuit in step 304, to determine whether or not tissue is being grasped.

The cumulative amount of energy delivered to the tissue during the sealing procedure may be stored as a total energy delivery variable (e.g., E_Total). E_Total may be determined in any suitable manner, for example, by integrating the output power over a power delivery time. In embodiments, the output power is sampled and totaled on a periodic basis to obtain an approximation of the total energy delivery. Microprocessor 5 may be configured to execute an interrupt service routine (ISR) that is programmed to periodically measure and sum or total the cumulative output power (E_Total). In embodiments, maximum energy delivery rate (e.g., E_Max), minimum energy delivery rate (e.g., E_Min), and average energy delivery rate (e.g., E_Avg) may also be computed and stored.

Thermal properties related to the tissue may be measured, recorded, and/or computed during the sealing process. Such properties may include, without limitation, total thermal energy sensed, which may be expressed as the sensed temperature integrated over the time of the procedure (e.g., T_total), maximum tissue temperature (e.g., T_Max), minimum tissue temperature (e.g., T_Min), and average tissue temperature (e.g., T_Avg). Fluid properties, i.e., a total quantity of fluid, which may be expressed as the sensed quantity of fluid integrated over the time of the procedure (e.g., F_Total), a maximum fluid quantity (e.g., F_Max), a minimum fluid quantity (e.g., F_Min), and an average fluid quantity of fluid (e.g., F_Avg), may additionally or alternatively be sensed, recorded and/or computed.

To determine whether there is an open circuit in step 304, the process determines whether the measured impedance is greater than a high impedance threshold or less than a low impedance threshold. If the measured impedance is greater than the high impedance threshold, an open circuit is detected.

Alternatively or additionally, the phase between voltage and current is measured by measuring the phase of the voltage with respect to the current or by measuring the phase of the current with respect to the voltage. The measured phase is then compared to lower and upper phase thresholds to determine whether there is a short circuit or an open circuit. The lower phase threshold may be from about 0.25 to about −1.6, in embodiments from about 0.1 to about −1.5. The upper phase threshold may be from about 1.1 to about 1.6, in embodiments, from about 1.25 to about 1.5. If the measured phase rises above the upper threshold, an open circuit is detected. If the measured phase falls below the lower threshold, a short circuit is detected.

If, in step 304, a short circuit is detected, e.g., the measured impedance falls below the low impedance threshold and/or the measured phase rises above the upper phase threshold, or if an open circuit is detected, e.g., the measured impedance rises above the high impedance threshold and/or the measured phase falls below the lower phase threshold, the control system or controller issues a regrasp alarm in step 360, and the tissue sealing procedure is exited in step 362. The process is optionally reinitiated at step 300 (as shown by the dashed arrow connecting step 362 to step 300). Otherwise, if no fault is detected in step 304 (i.e., no short and no open circuit is detected), the process starts the cook stage in step 306.

The control system then initiates application of RF energy (W_T) by delivering current to the tissue so that the power calculated by the control system tracks a non-linear polynomial power curve over time, in step 310. Once initiated, the control system increases the current so that the applied power tracks the polynomial power curve, in step 312, until one of two events occurs: (i) the maximum allowable value of a predetermined peak of the polynomial power curve is reached, in step 324; or (ii) the measured impendence value of the tissue exceeds sum of the lowest impedance value (Z_Low) and predetermined impedance rise value (Z_Rise), in step 322.

During the cook stage the control system continuously measures the tissue impedance (e.g., Z_T) in step 314. The control system also measures and stores the initial measured tissue impedance (e.g., EndZ_Offset). During the polynomial power curve portion of the cook stage, the stored lowest impedance value (Z_Low) is updated anytime the control system determines that a measured tissue impedance (Z_T) is lower than the previous measured lowest impedance value (Z_Low). In step 318, the control system compares the current measured tissue impedance (Z_T) with the stored lowest impedance value (Z_Low). If it is determined that the current measured tissue impedance (Z_T) is less than the previous measured lowest impedance value (Z_Low), this new value of the lowest impedance value (Z_Low) is stored in step 320, and the control system continues to control the power of the RF energy so that it tracks the polynomial power curve in step 312. If it is determined that the currently measured tissue impedance (Z_T) is greater than the previously measured lowest impedance value (Z_Low), the control system proceeds to step 322. In other words, during steps 314, 318 and 320, the control system waits for the tissue impedance to drop.

In steps 312, 314, 318, and 320, the control system controls the power of the RF energy to track the polynomial power curve (examples of which are shown in FIG. 4). When the currently measured tissue impedance (Z_T) is no longer less than the previously measured lowest impedance value (Z_Low) in step 318, the control system determines whether a tissue reaction has occurred, the control system uses two settings: (1) the lowest measured tissue impedance (Z_Low), and (2) the predetermined impedance rise value (Z_Rise), for the determination of a tissue reaction. The term "tissue reaction" is a point at which intracellular and/or extra-cellular fluid begins to boil and/or vaporize, resulting in an increase in tissue impedance. If the control system determines that the application of RF energy (W_T) has reached the maximum allowable power value, the control system maintains the output power at the maximum allowable power value until the tissue "reacts." This tissue reaction determination is based on whether the measured impedance (Z_T) is greater than a predetermined impedance threshold, such as the sum of the lowest impedance value (Z_Low) and the impedance rise value (Z_Rise) (i.e., the control system determines whether Z(t)>Z_Low+Z_Rise) (i.e., the control system determines whether Z(t)>Z_Low+Z_Rise) in step 322

At step 322, if it is determined that the measured impedance (Z_T) is greater than a predetermined impedance threshold, such as the sum of the lowest impedance value (Z_Low) and the impedance rise value (Z_Rise), the control system determines that a tissue reaction has occurred and exits the cook stage (proceeding to step 340) and initiates a cooling stage or phase, in step 342. The cooling stage may be an adaptive or a non-adaptive cooling stage, in which low power RF energy, e.g., RF energy having a power less than the peak power, is applied to tissue. The adaptive cooling stage may control power of the RF energy based on one or more characteristics of tissue being treated, such as in a dZ/dt control system, which varies the power of the RF energy so that changes in the measured impedance of the tissue tracks a desired changes in impedance over time. The non-adaptive cooling stage may apply power that is not based on one or more characteristics of tissue being treated, such as applying a constant low power or constantly decreasing power. If it is determined that a tissue reaction has not occurred, the control system determines whether the application of RF energy (W_T) has reached the peak of the polynomial power curve (W_Peak), in step 324.

In step 324, if the application of RF energy (W_T) has reached the peak of the polynomial power curve (W_Peak) (as indicated, for example, by reference numbers 408 and 410 of FIG. 4, for various jaw groups), the control system transitions the application of RF energy (W_T) to track a linear power curve, in step 326. If the application of RF energy (W_T) has not reached the peak of the polynomial power curve (W_Peak), in step 324, the control system continues tracking the application of RF energy (W_T) to the polynomial power curve, in step 312.

Following the application of RF energy (W_T) to track the polynomial power curve, in FIG. 3A, in step 326, the control system causes the application of RF energy (W_T) to track a linear power curve until one of two events occurs: (i) a maximum allowable power value is reached; or (ii) the "tissue reacts." In the event that the tissue reacts prior to reaching the maximum allowable power value, the energy required to initiate a tissue "reaction" has been attained and the control system exits the cook stage, in step 340, and transitions to a cooling stage, in step 342.

In step 328, the control system continuously measures the tissue impedance (Z_T) in step 314. During the polynomial power curve portion of the cook stage, the stored lowest impedance value (Z_Low) is updated anytime the control system determines that a measured tissue impedance (Z_T) is lower than the previous measured lowest impedance value (Z_Low). In step 332, the control system compares current measured tissue impedance (Z_T) with the stored lowest impedance value (Z_Low). If it is determined that the current measured tissue impedance (Z_T) is less than the previous measured lowest impedance value (Z_Low) this new value of the lowest impedance value (Z_Low) is stored, in step 334, and the applied power continues to track the linear power curve, in step 326. If it is determined that the current measured tissue impedance (Z_T) is greater than the previous measured lowest impedance value (Z_Low), the control system proceeds to step 336.

In steps 326, 328, 332, and 334, the control system controls the application of RF energy (W_T) to track the linear power curve (examples of which are shown in FIG. 4). Once the current measured tissue impedance (Z_T) is greater than the previous measured lowest impedance value (Z_Low), in step 332, the control system then determines whether a tissue reaction has occurred, the control system uses two settings: (1) the lowest measured tissue impedance (Z_Low) and (2) the predetermined impedance rise value (Z_Rise), for the determination of a tissue reaction. This tissue reaction determination is based on whether the measured impedance (Z_T) is greater than a predetermined impedance threshold, such as the sum of the lowest impedance value (Z_Low) and the impedance rise value (Z_Rise) (i.e., the control system determines whether Z(t)>Z_Low+Z_Rise), in step 336.

In step 322, if it is determined that the measured impedance (Z_T) is greater than a predetermined impedance threshold, such as the sum of the lowest impedance value (Z_Low) and the impedance rise value (Z_Rise), the control system exits the cook stage, in step 340, and initiates an adaptive cooling stage, in step 342. In step 338, if it is determined that the measured impedance (Z_T) is not greater than a predetermined impedance threshold, such as the sum of the lowest impedance value (Z_Low) and the impedance rise value (Z_Rise), the control system determines whether maximum cook stage timer has elapsed. If the maximum cook stage timer has not elapsed, in step 338, the application of RF energy (W_T) continues to track the linear power curve in step 326.

In step 338, if the maximum cook stage timer has elapsed before the measured impedance (Z_T) rises above the sum of the lowest impedance value (Z_Low) and the impedance rise value (Z_Rise), the control system or controller issues a regrasp alarm in step 364, and the tissue sealing procedure is exited in step 366. The process is optionally reinitiated at step 300 (as shown by the dashed arrow connecting step 366 to step 300).

After exiting the cook stage, in step 340, the control system transitions to a cooling stage, in step 342. One such example of a cooling stage is an impedance matching trajectory based on the actual impedance and the desired rate of change of impedance. The control system calculates a target impedance value at each time step based on a desired rate of change of impedance (dZ/dt). The desired rate of change of impedance may be stored as a setting in a configuration file and may be loaded. The desired rise of impedance may be selected manually by a user or automatically based on the tissue type and/or instrument characteristics. The control system then adjusts the power output from the output stage so that the measured tissue impedance tracks the impedance trajectory. The impedance trajectory includes an initial impedance value and extends over a period during which the tissue reaction is considered real and stable. In embodiments, the impedance trajectory may be in the form of a non-linear and/or quasi-linear curve.

The target impedance trajectory includes a plurality of a target impedance values at each time step. The control system adjusts the power level output from the output stage of the generator so that the measured tissue impedance tracks the target impedance trajectory. The control system determines whether tissue fusion is complete by determining whether the measured impedance rises above a predetermined threshold impedance and stays above the predetermined threshold impedance for a predetermined period. The predetermined threshold impedance may be defined as an impedance level above an initial impedance value (EndZ_Offset). Using the predetermined threshold impedance minimizes the likelihood of terminating electrosurgical energy early when the tissue is not properly or completely sealed. Further details regarding tissue sealing processes, including the cook stage, are found in commonly owned U.S. patent application Ser. No. 13/483,815, entitled "System and Method for Tissue Sealing," the entire contents of which are incorporated by reference herein.

FIG. 4 is a graph illustrating power control curves in two phases of the cook stage for two handsets of different sizes. Phase I includes a nonlinear power curve and Phase II includes a linear power curve. Both Groups 1 and 2 are shown in FIG. 4. In the embodiment shown in FIG. 4, the nonlinear power curve is a polynomial power curve. As shown in FIG. 4, the power control curves transition from the polynomial power curve to the linear power curve (e.g., a power ramp) at predetermined peak powers 408 and 410. Although the graph illustrating power control curves begins each curve at minimum start power 402 which is shown at 10 W, it is contemplated that minimum start power 402 may be lower depending on tissue and generator requirements. In embodiments, the polynomial power curve is customized for each handset to accommodate various jaw designs. For example, a higher power polynomial power curve may be used with larger jaw designs while lower power polynomial power curves may be used with smaller jaw designs.

During the cook stage it is contemplated that, as shown in FIG. 4, the maximum cook stage time (step 338 of FIG. 3B) is 4 seconds. Once the application of RF energy (W_T) has continued for 4 seconds the control system transitions from the cook stage, either issuing a regrasp alarm (step 364 of FIG. 3B) or determining that a tissue reaction has occurred (step 322 of FIG. 3A or step 336 of FIG. 3B). Additionally, the minimum amount of time for the application of RF energy (W_T) to continue in the cook stage is 0.5 seconds. If it is determined that a tissue reaction has occurred prior to the 0.5 seconds, the control system will also issue a regrasp alarm and optionally restart the procedure.

As shown in FIG. 4, Group 1 is an example used for handsets with larger jaws and Group 2 is an example used for handsets with smaller jaws. Peak of the polynomial power curve (W_Peak) 408 for Group 2 for the smaller jaw handsets reaches its peak prior to peak of the polynomial power curve (W_Peak) 410 for Group 2 for larger jaw handsets. The polynomial power curve can be configured to vary how aggressively the power is increased as shown in FIG. 4 to meet the specific devices sealing needs.

The power levels, shape, and length of the polynomial power curve may be determined based on parameters of the tissue or handset, such as tissue type, tissue hydration values, initial tissue impedance, volume of tissue between jaw members 110 and 120, and/or surface area of jaw members 110 and 120. For example, these parameters may be used to determine the predetermined peak power and the length of the polynomial power curve. The parameters of the polynomial power curve, such as the predetermined peak power and the length or duration of the polynomial power curve, may be adjusted based on desired cook stage results. The nonlinear power curve may include second-order, third-order, or greater orders of polynomial powers based on parameters of the tissue or handset described above. One example of a third-order polynomial is defined by the formula:

$$y = ax^3 + bx^2 + cx + d. \quad (1)$$

Through the selection of the coefficients a, b, c, and d, the curve of a graph plotting the polynomial power curve can be configured to match a desired slope, peak value, y-intercept, and curvature.

Although the example of the polynomial power curve portion of FIG. 4 is illustrated as a third order polynomial, greater orders may be used and via the selection of the coefficients used in the polynomial formula the curve may be configured, such that undesirable powers of the polynomial formula are removed through the use of a zero coefficient.

The curve of the polynomial power curve allows the cook stage to apply power to tissue slowly at first. The coefficients used in the polynomial power curve allow for customization of the power curve, such as the duration of time at which the power curve reaches the peak or the rate at which the slope of the polynomial power curve increases and/or decreases. One such example of a curve configuration is shown in FIG. 4, this curve has been customized to include an increasing power throughout the polynomial power curve portion via a slow start followed by an increased ramping and a slow ending. This slow application of power limits the risk of incidental impedance spikes due to over powering the tissue which may cause the control system to inadvertently leave the cook stage state prematurely before a sufficient amount of power has been applied to the tissue.

When the power of the electrosurgical energy output from the output stage reaches the predetermined peak powers 408 and 410, the control system controls the power of the electrosurgical energy according to the linear power curve. For example, the control system linearly ramps the power according to a desired slope as shown in FIG. 3B.

Referring back to FIG. 2, memory 6 includes any non-transitory computer-readable storage media for storing data and/or software that is executable by microprocessor 5 and which controls the operation of controller 4. In embodiments, memory 6 may include one or more solid-state storage devices such as flash memory chips. Alternatively or in addition to the one or more solid-state storage devices, memory 6 may include one or more mass storage devices connected to the microprocessor 5 through a mass storage controller (not shown) and a communications bus (not shown).

Although the description of computer-readable media refers to a solid-state storage, it should be appreciated by those skilled in the art that computer-readable storage media can be any available media that can be accessed by the microprocessor 5. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information.

The detailed embodiments described in the present application are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in virtually any appropriately detailed structure.

What is claimed is:

1. A method for performing an electrosurgical procedure comprising:
   supplying power to tissue from a radio frequency (RF) output stage of an electrosurgical generator;
   measuring impedance of the tissue;
   controlling the power supplied to track a nonlinear power curve until the power supplied has reached a peak power of the nonlinear power curve, wherein the nonlinear power curve is a third-order polynomial defined by a plurality of coefficients;
   performing a determination whether a tissue reaction has occurred based on the measured impedance of the tissue; and
   controlling the power supplied according to a cooling phase based on the determination that the tissue reaction has occurred.

2. The method according to claim 1, further comprising:
   controlling the power supplied from the RF output stage to track a linear power curve based on a peak power determination that the power supplied from the RF output stage has reached the peak power of the nonlinear power curve.

3. The method according to claim 2, wherein the controlling of the supplied power includes storing, in a memory, a look-up table including a plurality of nonlinear power curves, a plurality of linear power curves, and a plurality of sizes of electrodes of electrosurgical instruments usable with the electrosurgical generator.

4. The method according to claim 3, further comprising:
   receiving an electrode size; and
   selecting the nonlinear power curve from the plurality of nonlinear power curves and the linear power curve from the plurality of linear power curves based on the electrode size.

5. The method according to claim 2, further comprising:
   adjusting a parameter of the linear power curve based on a surface area of an electrode of an electrosurgical instrument usable with the electrosurgical generator, wherein the parameter of the linear power curve is selected from the group consisting of slope and duration.

6. The method according to claim 5, wherein the duration of the linear power curve is zero.

7. The method according to claim 5, wherein the larger the surface area of the electrode, the shorter the duration and larger the slope of the linear power curve.

8. The method according to claim 5, wherein the smaller the surface area of the electrode, the longer the duration and smaller the slope of the linear power curve.

9. The method according to claim 1, further comprising adjusting a parameter of the nonlinear power curve based on a surface area of an electrode of an electrosurgical instrument usable with the electrosurgical generator.

10. The method according to claim 9, wherein the parameter of the nonlinear power curve is selected from the group consisting of starting power, duration, shape, slopes, peak power, and combinations thereof.

11. The method according to claim 9, wherein a duration and a peak power of the nonlinear power curve are proportional to the surface area of the electrode.

12. The method according to claim 9, wherein the electrosurgical instrument includes a Radio Frequency Identification tag storing the parameter of the nonlinear power curve.

13. The method according to claim 1, further comprising: storing, in a memory, a look-up table including a plurality of nonlinear power curves and a plurality of sizes of electrodes of an electrosurgical instrument usable with the electrosurgical generator.

14. The method according to claim 13, further comprising:
receiving an electrode size and selecting a nonlinear power curve from the plurality of nonlinear power curves based on the electrode size.

15. The method according to claim 1, further comprising: performing a calculation of a minimum impedance based on the measured impedance.

16. The method according to claim 15, further comprising: performing the determination based on the minimum impedance and a rise in the measured impedance of the tissue being treated.

17. The method according to claim 1, further comprising:
performing a time-based tissue reaction determination to determine whether the tissue reaction has occurred within a first period; and
stopping the power supplied from the RF output stage, and issuing a re-grasp message, based on the time-based tissue reaction determination that the tissue reaction has occurred within the first period.

18. The method according to claim 1, further comprising:
performing a time-based tissue reaction determination to determine whether the tissue reaction has occurred within a second period; and
controlling the power supplied from the RF output stage to restart tracking of the nonlinear power curve based on the time-based tissue reaction determination that the tissue reaction has not occurred within the second period.

* * * * *